US00PP26883P2

(12) United States Plant Patent
Pounders et al.

(10) Patent No.: US PP26,883 P2
(45) Date of Patent: Jun. 28, 2016

(54) AZALEA PLANT NAMED 'AZ 56'

(50) Latin Name: *Rhododendron hybrida*
Varietal Denomination: AZ 56

(71) Applicants: The United States of America, as represented by the Secretary of Agriculture, Washington, DC (US); Capstone Plants Inc., Grand Saline, TX (US)

(72) Inventors: Cecil T Pounders, Poplarville, MS (US); James B Berry, Mineola, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 78 days.

(21) Appl. No.: 14/121,951

(22) Filed: Nov. 6, 2014

(51) Int. Cl.
*A01H 5/00* (2006.01)

(52) U.S. Cl.
USPC ..... Plt./239

(58) Field of Classification Search
USPC ..... Plt./239
See application file for complete search history.

*Primary Examiner* — Annette Para
(74) *Attorney, Agent, or Firm* — Penny J. Aguirre

(57) ABSTRACT

A new cultivar of hybrid Azalea named 'AZ 56' that is characterized by its upright, compact, densely branched plant habit, its pink flowers with deep purple flecks on the upper surface of the petals, its two distinct bloom cycles with a strong bloom period early to mid-April followed by a seconding bloom period in early fall in Mississippi, its disease-free, mature foliage that is dark green in color and retained during the winter when it takes on a purple blush, its high tolerance to seasonal temperature fluctuations from 38° C. (100° F.) in the summer to as low as −10° C. (14° F.) in the winter, and its ease of propagation by softwood stem cuttings.

2 Drawing Sheets

Botanical classification: *Rhododendron hybrida.*
Cultivar designation: 'AZ 56'.

BACKGROUND OF THE INVENTION

The present invention relates to a new and distinct cultivar of *Rhododendron* plant of hybrid origin, botanically known as *Rhododendron hybrida* 'AZ 56' and will be referred to hereafter by its cultivar name, 'AZ 56'. 'AZ 56' is a new cultivar of evergreen Azalea grown for use as a landscape plant.

The new cultivar was developed through an on-going breeding program conducted by the Inventors in Poplarville, Miss., USA. The objectives of the breeding program are to develop new cultivars of Azalea that exhibit tolerance to environmental stresses and disease resistance combined with unique flower colors and extended bloom periods.

The new cultivar arose from a cross made in the spring of 2005 between 'Tom Dodd 28' (not patented) as the female parent and 'Red Slipper' (not patented) as the male parent. The Inventors selected 'AZ 56' as a single unique plant amongst the seedlings that resulted from the above cross in June of 2008.

Asexual propagation of the new cultivar was first accomplished by softwood stem cuttings in Poplarville, Miss. in 2008 by one of the Inventors. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics 'AZ 56'. These attributes in combination distinguish 'AZ 56' as a new and distinct cultivar of Azalea.

1. 'AZ 56' exhibits an upright, compact, densely branched plant habit.
2. 'AZ 56' exhibits pink flowers with deep purple flecks on the upper surface of the petals.
3. 'AZ 56' exhibits two distinct bloom cycles with a strong bloom period early to mid-April followed by a seconding bloom period in early fall in Mississippi.
4. 'AZ 56' exhibits disease-free, mature foliage that is dark green in color and retained during the winter when it takes on a purple blush.
5. 'AZ 56' exhibits a high tolerance to seasonal temperature fluctuations from 38° C. (100° F.) in the summer to as low as −10° C. (14° F.) in the winter.
6. 'AZ 56' is readily propagated by softwood stem cuttings.

The female parent of 'AZ 56', 'Tom Dodd 28', differs from 'AZ 56' in having poor winter foliage retention, in having an open growth habit, and in having very little rebloom. The male parent of 'AZ 56', 'Red Slipper', differs from 'AZ 56' in having reduced cold hardiness, in having flowers that are purplish-red in color, and in having larger flowers with petaloids present. 'AZ 56' can also be most closely compared to the azalea cultivars 'August to Frost' (not patented) and 'MN1HAR010' (U.S. Plant Pat. No. 22,545). 'August to Frost' is similar to 'AZ 56' in having a fall bloom cycle, in being well adapted to plant hardiness zone 7, and in being tolerant to pests common to Azalea cultivars. 'August to Frost' differs from 'AZ 56' in having flowers that are white in color, in having an open spreading plant habit, in lacking a spring bloom cycle, and in having no winter bloom buds. 'MN1HAR010' is similar to 'AZ 56' in being easily propagated and in growing and flowering well in containers in moderate shade. 'MN1HAR010' differs from 'AZ 56' in having flowers that are salmon in color, in being less tolerant to full sun and high temperatures, and in having foliage that lacks a purple blush color in the winter.

BRIEF DESCRIPTION OF THE DRAWINGS

The accompanying colored photographs illustrate the overall appearance and distinct characteristics of the new Azalea. The photographs were taken of 10 month-old plants of the new cultivar as grown outdoors and in cold frame houses in three-gallon containers in Grand Saline, Tex.

The photograph in FIG. 1 provides a side view of 'AZ 56' in bloom.

Figure 1:
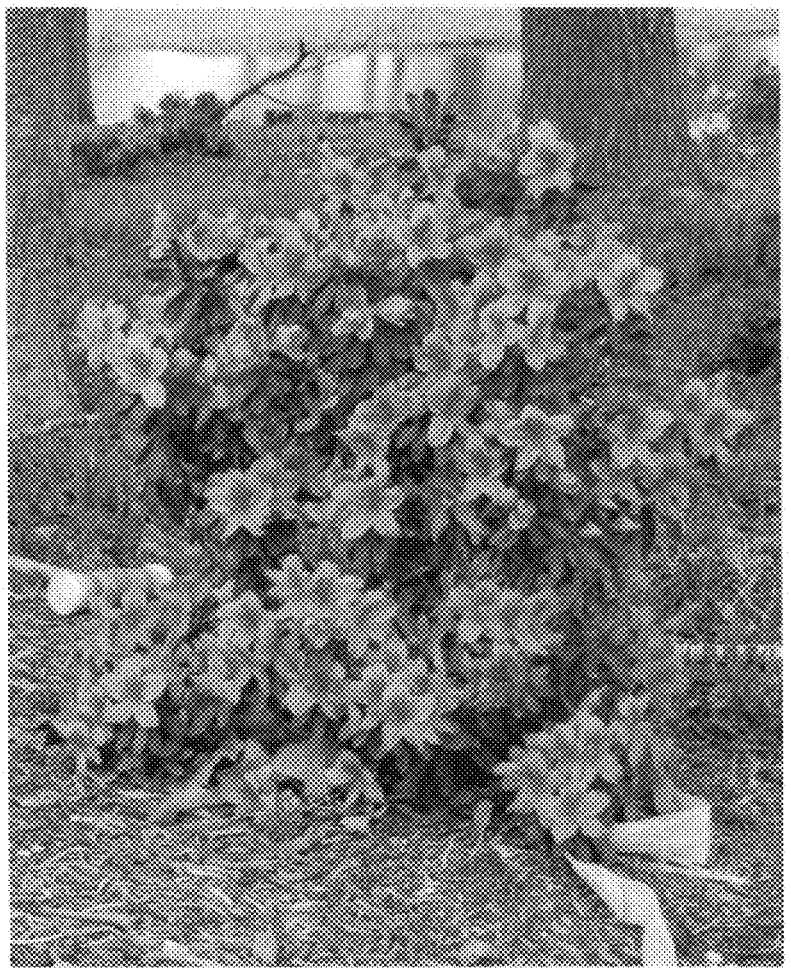
Figure 2:
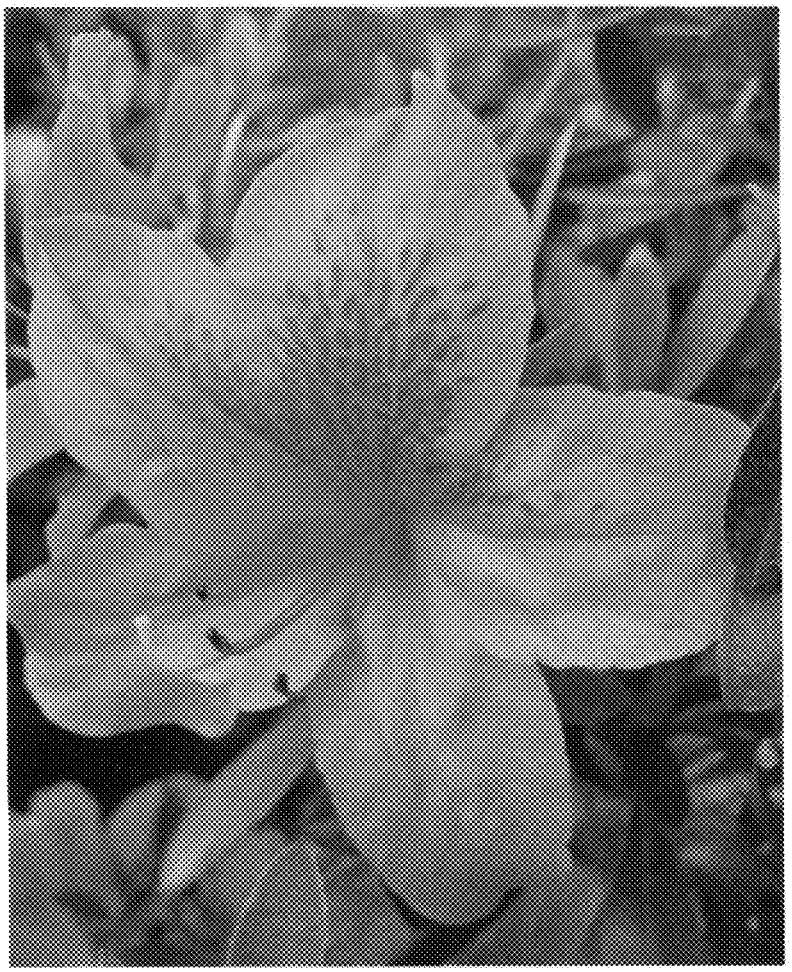

The photograph in FIG. 2 provides a close-up view of an inflorescence of 'AZ 56'.

The colors in the photographs are as close as possible with the photographic and printing technology utilized and the color values cited in the detailed botanical description accurately describe the colors of the new Azalea.

DETAILED BOTANICAL DESCRIPTION OF THE PLANT

The following is a detailed description of 10 month-old plants of the new cultivar as grown outdoors in three-gallon containers in Grand Salinas, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

- *Blooming period*.—Two weeks in the beginning to mid-April and again in early fall in Mississippi, USA.
- *Plant type*.—Evergreen shrub.
- *Plant habit*.—Upright, compact, densely branched.
- *Height and spread*.—An average of 90 cm in height and width.
- *Cold hardiness*.—At least in U.S.D.A. Zone 7.
- *Diseases and pests*.—Strong tolerance to diseases and pest common to azaleas has been observed; tolerance to root and crown rot caused by *Phytophthora* sp., petal blight caused by *Ovulinia azalea*, and leaf gall caused by *Exobasidium vaccinii* and tolerance to *Stephanitis pyrioides* (Azalea lace bug).
- *Root description*.—Abundant, fibrous, moderately dense.
- *Propagation*.—Softwood cuttings.
- *Root development*.—Roots initiate in 4 weeks and fully develop a 50 cell liner in about 12 weeks.
- *Growth rate*.—Vigorous.

Stem description:

- *Shape*.—Round.
- *Stem color*.—New growth; a blend of 145A and 166A to 166B, mature wood; 166A to 166B.
- *Stem size*.—Main stems; an average of 7 cm in length and 9 mm in width, lateral stems; an average of 15 cm in length and 4 mm in diameter, tertiary stems; an average of 13 cm in length and 2 mm in diameter.
- *Stem surface*.—New growth; very pubescent, mature wood; ridged bark, exfoliating.
- *Stem aspect*.—Held at an average angle of 5° to 10° (0°=vertical).
- *Stem strength*.—Strong.
- *Branching*.—Self-branching, an average of 3 main stems and 6 lateral branches per main stem in a five-gallon container.
- *Internode*.—Average of 1.5 cm.

Foliage description:

- *Leaf shape*.—Oblanceolate.
- *Leaf division*.—Simple.
- *Leaf base*.—Cuneate.
- *Leaf apex*.—Acute with very tip mucronate.
- *Leaf venation*.—Pinnate, upper surface; 139A in color, lower surface; 144A to 144B in color.
- *Leaf margins*.—Entire.
- *Leaf attachment*.—Petiolate.
- *Leaf arrangement*.—Alternate.
- *Leaf aspect*.—Held horizontal to upright.
- *Leaf surface*.—Upper surface; glabrous and very pubescent covered with hairs an average of 1 mm in length and NN155D in color, lower surface; glabrous and slightly shiny.
- *Leaf color*.—Young leaves upper and lower surface; 143A to 143C, mature leaves upper surface; 139A, mature leaves lower surface; 144A to 144B, winter color upper surface 139A and suffused with 187A, winter lower surface; 138A.
- *Leaf size*.—Average of 3 cm in length, and 9 mm in width.
- *Leaf quantity*.—About 60 leaves per lateral branch 15 cm in length.
- *Petioles*.—Average of 5 mm in length and 1 mm in diameter, a blend of 144C and 166B in color, pubescent surface.

Flower description:

- *Inflorescence type*.—Flowers are solitary.
- *Lastingness of flowers*.—About 10 days, self cleaning.
- *Flower size*.—An average of 5 cm in depth and 7 cm in diameter.
- *Flower fragrance*.—None.
- *Flower shape*.—Tubular base with flared petal lobes.
- *Flower number*.—Average of 2 per lateral stem.
- *Flower aspect*.—Upright and outwards.
- *Flower bud*.—Ovate to oblanceolate in shape, an average of 40 mm in depth and 10 mm in diameter, apex; acute, color; 68A to 68B suffused with 184B near the base.
- *Flower attachment*.—Pedicel.
- *Petal number*.—5.
- *Petal shape*.—Elliptic.
- *Petal color*.—Upper surface; 68A with internal freckles 60A to 60B and lower suface; 68B.
- *Petal surface*.—Both surfaces glabrous.
- *Petal margins*.—Entire and slightly wavy.
- *Petal apex*.—Acute.
- *Petal base*.—Fused.
- *Petal size*.—Average of 5 cm in length and 2.5 cm in width.
- *Sepal number*.—5.
- *Sepal shape*.—Oblong to oval.
- *Sepal margin*.—Entire.
- *Sepal size*.—Average of 6 mm in length and 2 mm in width.
- *Sepal aspect*.—Upright.
- *Sepal surface*.—Upper surface; pubescent and lower surface; glabrous.
- *Sepal apex*.—Acute.
- *Sepal base*.—Fused.

*Sepal color*.—Upper and lower surface; 143A to 143B.

*Calyx*.—Campanulate in shape, average of 6 mm in length and 5 cm in diameter.

*Peduncles*.—An average of 14 mm in length and 2 mm in diameter, 144A with a stripe 184 in color, flexible strength, pubescent surface, held upright.

*Pedicels*.—None.

Reproductive organs:

*Gynoecium*.—1 Pistil, stigmas; clavate shaped, 144B in color, style; 4 cm in length and 63B with 138D near the base color, ovary; conical in shape, 5 mm in length and 2.5 mm in width, 136A in color, heavily pubescent surface.

*Androecium*.—Stamens; average of 5, weak in strength, 3.8 cm in length and 0.5 mm in width, 63B to 63D in color, anthers; dorsifixed 187B in color; pollen very sparse in quantity.

*Fruit/seeds*.—None observed.

It is claimed:

1. A new and distinct cultivar of Azalea plant named 'AZ 56' as herein illustrated and described.

* * * * *